(12) United States Patent
Moon et al.

(10) Patent No.: US 12,266,448 B2
(45) Date of Patent: Apr. 1, 2025

(54) MEDICAL INDICATION DETERMINATION USING HETEROGENEOUS DATA IN A CLINICAL DECISION SUPPORT SYSTEM

(71) Applicant: Change Healthcare Holdings LLC, Nashville, TN (US)

(72) Inventors: Changsung Moon, Kirkland, WA (US); Feili Yu, Shoreline, WA (US)

(73) Assignee: Change Healthcare Holdings LLC, Nashville, TN (US)

( * ) Notice: Subject to any disclaimer, the term of this patent is extended or adjusted under 35 U.S.C. 154(b) by 360 days.

(21) Appl. No.: 17/538,273

(22) Filed: Nov. 30, 2021

(65) Prior Publication Data
US 2023/0170092 A1 Jun. 1, 2023

(51) Int. Cl.
*G16H 50/20* (2018.01)
*G06F 16/334* (2025.01)

(52) U.S. Cl.
CPC ........... *G16H 50/20* (2018.01); *G06F 16/334* (2019.01)

(58) Field of Classification Search
CPC ........ G16H 50/20; G16H 50/70; G16H 70/20; G16H 10/60; G16H 40/20; G06F 16/334
See application file for complete search history.

(56) References Cited

U.S. PATENT DOCUMENTS

2021/0304857 A1* 9/2021 Johansson ................ G06N 3/08

* cited by examiner

*Primary Examiner* — Meredith A Long
(74) *Attorney, Agent, or Firm* — Myers Bigel, P.A.

(57) ABSTRACT

A method includes receiving input information associated with an examination order for a patient, the input information comprising first information associated with a plurality of variables and second information associated with a free-text query for the examination order; embedding the plurality of variables to generate a plurality of input variable vectors, respectively; embedding the free-text query for the order to generate a free-text query vector; aggregating the plurality of input variable vectors with the free-text query vector to generate an examination order vector; and determining, using an artificial intelligence engine, a medical indication corresponding to the examination order based on the examination order vector.

17 Claims, 7 Drawing Sheets

MEDICAL INDICATION DETERMINATION USING HETEROGENEOUS DATA IN A CLINICAL DECISION SUPPORT SYSTEM

FIELD

The present inventive concepts relate generally to health care systems and services and, more particularly, medical indication selection by a health care provider as a basis for performing and/or prescribing an order, such as a test, procedure, surgery, and/or medication.

BACKGROUND

As part of a workflow for administering care to patients, health care service providers place orders through Electronic Medical Records (EMR)/order entry systems. An order may be, for example, instructions to perform a test or procedure and/or may be a prescription for a medication or medical device. In addition to entering the order, a health care service provider may also be required to provide a medical indication for the order. A medical indication may be viewed as a reason to issue an order, e.g., a criterion for when it is appropriate to perform a particular test, prescribe a particular medication, etc. There are thousands of medical indications for health care service providers to choose from when placing an order. These medical indications may also be associated with Appropriate Use Criteria (AUC), which are developed by various medical specialty societies. Government regulations, such as those associated with Medicare, for example, may require health care service providers ordering particular exams for Medicare patients to consult AUC through a qualified decision support mechanism. This may require a health care service provider to search through a large number of possible indications as the qualified decision support mechanisms typically generate a lengthy list of proposed indications based on a patient's age and gender along with the order. Additional information associated with a patient's medical record and care may not be considered by these decision support mechanisms.

SUMMARY

According to some embodiments of the inventive concept, a method comprises: receiving input information associated with an examination order for a patient, the input information comprising first information associated with a plurality of variables and second information associated with a free-text query for the examination order; embedding the plurality of variables to generate a plurality of input variable vectors, respectively; embedding the free-text query for the order to generate a free-text query vector; aggregating the plurality of input variable vectors with the free-text query vector to generate an examination order vector; and determining, using an artificial intelligence engine, a medical indication corresponding to the examination order based on the examination order vector.

In other embodiments, the method further comprises generating a knowledge graph that associates the plurality of variables with a plurality of medical indications.

In still other embodiments, the artificial intelligence engine comprises a multi-layer neural network, the method further comprising: assigning the plurality of variables and the free-text query for the order to nodes of an input layer of the multi-layer neural network, respectively; and assigning the plurality of medical indications to nodes of an output layer of the multi-layer neural network, respectively.

In still other embodiments, the method further comprises: initializing the nodes of the input layer of the multi-layer neural network with the plurality of input variable vectors and the free-text query vector; embedding the plurality of medical indications to generate a plurality of medical indication vectors, respectively; and initializing the nodes of the output layer of the multi-layer neural network with the plurality of medical indication vectors. Determining, using the artificial intelligence engine, the medical indication comprises: aggregating the plurality of medical indication vectors to generate an aggregated medical indication vector; and generating, using the multi-layer neural network, a similarity score between the examination order vector and the aggregated medical indication vector.

In still other embodiments, generating, using the multi-layer neural network, the similarity score comprises generating a plurality of similarity scores between the examination order vector and the plurality of medical indication vectors, respectively.

In still other embodiments, generating the plurality of similarity scores comprises generating a plurality of cosine similarity scores between the examination order vector and the plurality of medical indication vectors, respectively.

In still other embodiments, the medical indication corresponding to the examination order comprises one of the plurality of medical indications having a highest ranked cosine similarity score associated therewith.

In still other embodiments, the method further comprises: communicating to an examination order entry system for entry therein, without input from a provider, an automatic selection of the one of the plurality of medical indications having the highest ranked cosine similarity score associated therewith when the highest ranked cosine similarity score exceeds a threshold.

In still other embodiments, the method further comprises: communicating to the examination order entry system N of the plurality of medical indications having N highest ranked cosine similarity scores associated therewith, respectively, when the highest ranked cosine similarity score does not exceed the threshold, wherein N is less than a total number of the plurality of medical indications.

In still other embodiments, the threshold is a first threshold, the method further comprises communicating to the examination order system an indication that none of the plurality of medical indications is applicable to the examination order when the highest ranked cosine similarity score is less than a second threshold.

In still other embodiments, the plurality of variables comprises one or more variables associated with the patient including an age, a gender, a problem list, an encounter diagnosis, a patient class, and/or a medical center department; the plurality of variables comprises one or more variables associated with a provider including a provider identifier and/or a provider specialty; and the plurality of variables comprises one or more variables associated with an order including an order name, order identification, order modality, order contrast, and/or body area identification.

In some embodiments of the inventive concept, a system comprises a processor; and a memory coupled to the processor and comprising computer readable program code embodied in the memory that is executable by the processor to perform operations comprising: receiving input information associated with an examination order for a patient, the input information comprising first information associated with a plurality of variables and second information associated with a free-text query for the examination order; embedding the plurality of variables to generate a plurality of input variable vectors, respectively; embedding the free-text query for the order to generate a free-text query vector; aggregating the plurality of input variable vectors with the free-text query vector to generate an examination order vector; and determining, using an artificial intelligence engine, a medical indication corresponding to the examination order based on the examination order vector.

In further embodiments, the operations further comprise: generating a knowledge graph that associates the plurality of variables with a plurality of medical indications.

In still further embodiments, the artificial intelligence engine comprises a multi-layer neural network, the operations further comprising: assigning the plurality of variables and the free-text query for the order to nodes of an input layer of the multi-layer neural network, respectively; and assigning the plurality of medical indications to nodes of an output layer of the multi-layer neural network, respectively.

In still other embodiments, the operations further comprise: initializing the nodes of the input layer of the multi-layer neural network with the plurality of input variable vectors and the free-text query vector; embedding the plurality of medical indications to generate a plurality of medical indication vectors, respectively; and initializing the nodes of the output layer of the multi-layer neural network with the plurality of medical indication vectors. Determining, using the artificial intelligence engine, the medical indication comprises: aggregating the plurality of medical indication vectors to generate an aggregated medical indication vector; and generating, using the multi-layer neural network, a similarity score between the examination order vector and the aggregated medical indication vector.

In still other embodiments, generating, using the multi-layer neural network, the similarity score comprises generating a plurality of similarity scores between the examination order vector and the plurality of medical indication vectors, respectively.

In some embodiments of the inventive concept, a computer program product comprises a non-transitory computer readable storage medium comprising computer readable program code embodied in the medium that is executable by a processor to perform operations comprising: receiving input information associated with an examination order for a patient, the input information comprising first information associated with a plurality of variables and second information associated with a free-text query for the examination order; embedding the plurality of variables to generate a plurality of input variable vectors, respectively; embedding the free-text query for the order to generate a free-text query vector; aggregating the plurality of input variable vectors with the free-text query vector to generate an examination order vector; and determining, using an artificial intelligence engine, a medical indication corresponding to the examination order based on the examination order vector.

In other embodiments, the operations further comprise: generating a knowledge graph that associates the plurality of variables with a plurality of medical indications.

In still other embodiments, the artificial intelligence engine comprises a multi-layer neural network, the operations further comprising: assigning the plurality of variables and the free-text query for the order to nodes of an input layer of the multi-layer neural network, respectively; and assigning the plurality of medical indications to nodes of an output layer of the multi-layer neural network, respectively.

In still other embodiments, the operations further comprise: initializing the nodes of the input layer of the multi-layer neural network with the plurality of input variable vectors and the free-text query vector; embedding the plurality of medical indications to generate a plurality of medical indication vectors, respectively; and initializing the nodes of the output layer of the multi-layer neural network with the plurality of medical indication vectors. Determining, using the artificial intelligence engine, the medical indication comprises: aggregating the plurality of medical indication vectors to generate an aggregated medical indication vector; and generating, using the multi-layer neural network, a similarity score between the examination order vector and the aggregated medical indication vector.

Other methods, systems, articles of manufacture, and/or computer program products according to embodiments of the inventive concept will be or become apparent to one with skill in the art upon review of the following drawings and detailed description. It is intended that all such additional systems, methods, articles of manufacture, and/or computer program products be included within this description, be within the scope of the present inventive subject matter and be protected by the accompanying claims.

BRIEF DESCRIPTION OF THE DRAWINGS

Other features of embodiments will be more readily understood from the following detailed description of specific embodiments thereof when read in conjunction with the accompanying drawings, in which.

DETAILED DESCRIPTION

Figure 1:
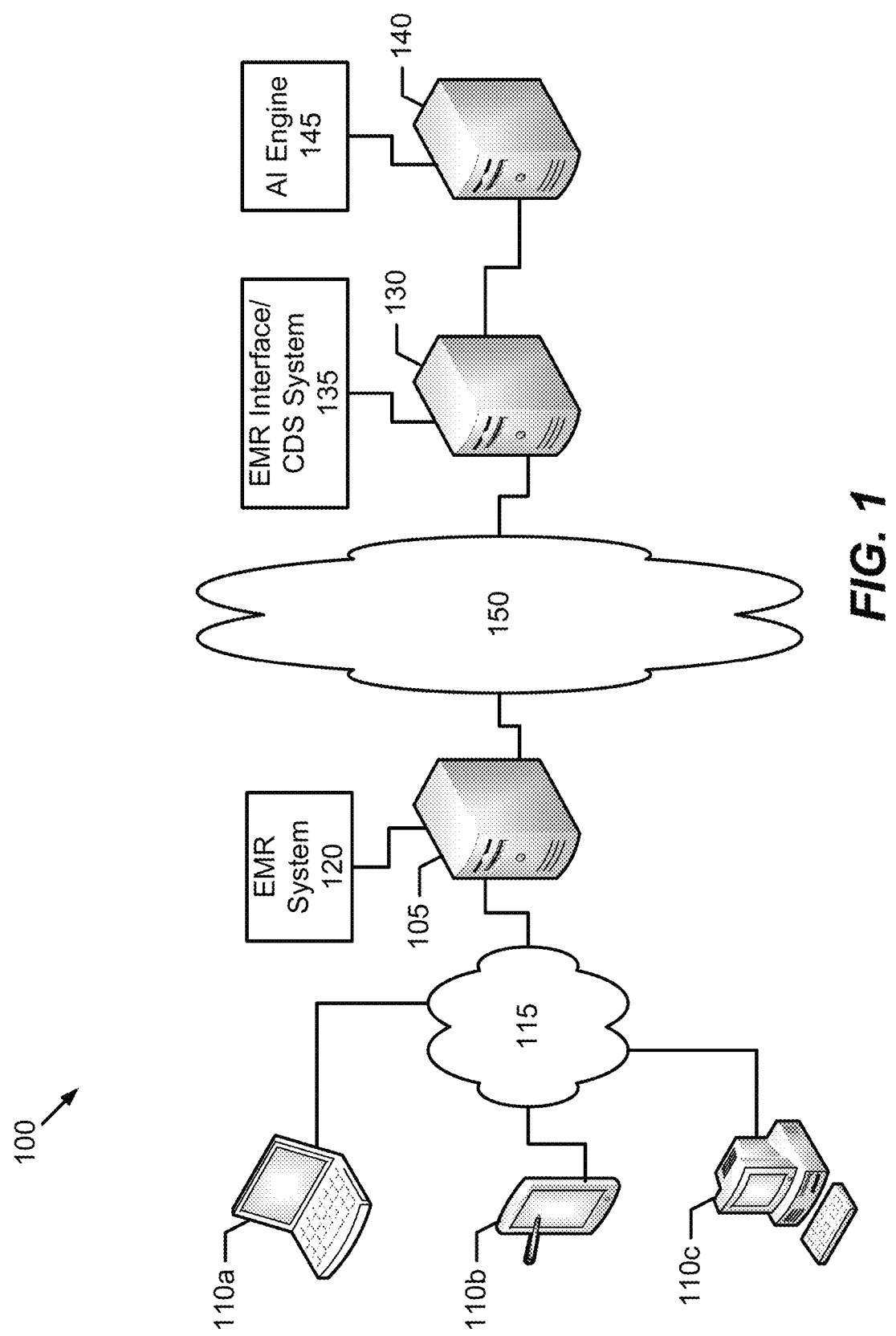
FIG. 1 is a block diagram that illustrates a communication network including an Artificial Intelligence (AI) assisted clinical decision support support system for determining a medical indication for an order in accordance with some embodiments of the inventive concept.

In the following detailed description, numerous specific details are set forth to provide a thorough understanding of embodiments of the inventive concept. However, it will be understood by those skilled in the art that embodiments of the inventive concept may be practiced without these specific details. In some instances, well-known methods, procedures, components, and circuits have not been described in detail so as not to obscure the inventive concept. It is intended that all embodiments disclosed herein can be implemented separately or combined in any way and/or combination. Aspects described with respect to one embodiment may be incorporated in different embodiments although not specifically described relative thereto. That is, all embodiments and/or features of any embodiments can be combined in any way and/or combination.

As used herein, the term "medical indication" refers to a valid reason to order a treatment or procedure, such as, but not limited to, a test, surgery, medication, and medical device. There can be multiple medical indications to order or use a particular treatment or procedure.

Embodiments of the inventive concept are described herein in the context of an artificial intelligence engine comprising a multi-layer neural network and/or a natural language processor. It will be understood that other types of artificial intelligence systems can be used in other embodiments of the artificial intelligence engine including, but not limited to, machine learning systems, deep learning systems, and/or computer vision systems. Moreover, it will be understood that the multi-layer neural network described herein is a multi-layer artificial neural network comprising artificial neurons or nodes and does not include a biological neural network comprising real biological neurons.

Some embodiments of the inventive concept stem from a realization that clinical decision support mechanisms and/or medical indication selection algorithms use a limited amount of information associated with a patient, such as age, gender, and an order description, when presenting a health care services provider ("provider") with a list of possible medical indications for an order. This can result in the provider needing to review numerous possible medical indications to select one that best supports a particular order. Some embodiments of the inventive concept may provide an Artificial Intelligence (AI) assisted clinical decision support system that takes advantage of a variety of different information available that is associated with the patient and/or order to provide a more accurate and focused list of possible medical indications for a given order. Moreover, the information that is input to the clinical decision support system may comprise heterogenous data, such as numerical information, categorical information, and even free text query information generated by one or more medical practitioners. For example, in some embodiments, the AI assisted clinical decision support system may use input information associated with the patient, the provider, and/or the order as a basis for generating one or more possible medical indications corresponding to the order. This patient information may include, but is not limited to, age, gender, problem list, encounter diagnosis, patient class, and/or a medical center department. The provider information may include, but is not limited to, a provider identifier and/or a provider specialty. In accordance with various embodiments of the inventive concept, the scope of recognition for the provider identifier may span a range of possibilities. For example, the provider identifier may be a site-specific (e.g., hospital or medical practice specific), regional, and/or national identifier. The order information may include, but is not limited to, an order name, order identification, order modality, order contrast, body area identification, and/or a free-text query or reason for the order (e.g., pain, intoxicated, altered mental status, etc.). The various input information variables and may be embedded into input variable vectors and the free-text query for the order may also be embedded into a free-text query vector. The input variable vectors and the free-text query vector may be aggregated to form an examination order vector, which can be used as input for training the AI assisted clinical decision support system as well as making a medical indication determination when operating the AI assisted clinical decision support system in inference mode using new input information or data.

Some clinical decision support systems use separate AI engines or models for different types of input information. For example, one AI engine or model may be used for generating an inference or recommendation based on the patient, provider, and some of the order information while a second AI engine or model may be used for generating an inference or recommendation based on free-text query information associated with an order. The outputs of these two different AI engines or models are then combined to generate a final prediction or recommendation. The technologies used in the different AI engines or models is typically different, however. For example, the first AI engine or model that processes patient, provider, and some of the order information may use traditional machine learning and/or a neural network while the second AI engine or model that processes the free-text order information may use natural language processing. The outputs of the two AI engines or models (e.g., probability scores for various medical indication or reason codes) may be combined using a weighted average. Combining the outputs of the two AI engines models, which are trained separately using different types of features and technologies, may be problematic. For example, the two different AI engines or models may use different scales or scores. In addition, the two different AI engines or models do not take into account the other AI engine or model when they are trained. In other words, there is no correlation between the outcomes of the two different AI engines or models. Thus, the accuracy in combining the results of the two different AI engines or models may be suspect. Aggregating the input variable vectors and the free-text query vector to form an examination order vector, which can be used as input for training an AI assisted clinical decision support system using a single AI engine or model may improve the accuracy of potential medication indications that are generated as an output when operating the AI assisted clinical decision support system in inference or recommendation mode.

In some embodiments of the inventive concept, the AI engine used to support the medical indication selection process may include two components: a multi-layer neural network and a natural language processor, which are used to determine one or more medical indications that may be applicable to an order based on evidence-based guidelines provided by, for example, one or more medical specialty societies, medical schools, government regulations, and the like. These guidelines may be used in the training, knowledge base, and/or vocabulary for the neural network and the content similarity engine. The neural network may be used to process the patient, provider, and order information, including the free-text reason for the order, which are aggregated as an examination order vector, to generate one or more possible medical indications for an order. These possible medical indications may have similarity scores associated therewith. These scores may be generated, for example, using a similarity analysis between embedded vectors corresponding to various medical indications and the examination order vector. In some embodiments, a cosine similarity function may be used to perform the similarity analysis. The similarity score is indicative of the probability that the medical indication is applicable to the order. When a particular medical indication has a probability that exceeds a defined threshold for an order, then the medical indication may be communicated, for example, to an order entry system and/or an electronic medical record (EMR) system for automatic entry therein, thereby alleviating the provider of having to select a medical indication for the order. Thus, some embodiments of the inventive concept may provide a medical service provider relief from the task of reviewing hundreds or thousands of possible medical indications for an order as the selection may be completely automated based on the available patient, provider and/or order information.

There may not be a single medical indication, however, having a probability applicability to the order that exceeds the defined threshold for automatic selection. Embodiments of the inventive concept may, however, narrow down the list of possible medical indications for a provider to consider by presenting the provider with a list of medical indications having the N highest probabilities of being applicable to the order based on their scores. The number N may be selected to provide a manageable number of medical indications for a provider to review and may also be determined based on cut-offs or gaps between the scores associated with possible medical indications. For example, if there is a relatively small gap between the probabilities associated with the top five possible medical indications, but there is a large gap between the fifth highest probability and the sixth highest probability, then N may be set to five to communicate the top five medical indications to the order entry system/EMR system for review and selection by the provider.

In some circumstances, however, the probabilities associated with the highest probable medical indications may be relatively low. This may indicate that the neural network was unable to find a medical indication for an order that satisfies the evidence-based guidelines on which the neural network is trained. In accordance with various embodiments of the inventive concept, various metrics can be used that measure a confidence level for a medical indication prediction. In some embodiments, a highest one of the probabilities associated with the possible indications may be compared with a defined threshold. When the probability is below the defined threshold, then it can be concluded that no medical indication was found for that particular order. In other embodiments, when a sum of the probabilities of the K possible medical indications having the highest probabilities is below a defined threshold, then it can be concluded that no medical indication was found for that particular order. This "no result" outcome can be communicated to the order entry system/EMR system allowing the provider to select a medical indication manually. In some embodiments, these threshold determinations may be made by a clinical decision support system that can communicate with an order entry system/EMR system based on the probabilities generated by the AI engine. In other embodiments, the AI engine may perform the threshold comparisons and communicate the results to the clinical decision support system.

As described above, the AI engine may also include a natural language processor. The natural language processor may be used to analyze input information, such as a free-text query for an order, categorical input variables, and medical indications to generate embedding therefor. An embedding is a learned continuous vector representation of a discrete variable. An embedding can reduce the dimensionality of categorical variables and represent the categories in the transformed vector space.

Thus, the AI assisted clinical decision support system, according to some embodiments of the inventive concept, may allow possible medical indications to be identified for an order based on evidence-based guidelines established by accepted authorities. These accepted authorities may include, but are not limited to, recognized or credentialed medical organizations, such as, for example, medical societies associated with various practice specialties, academic institutions, commercial institutions, such as pharmaceutical and/or hospital product companies, governmental organization(s), and/or other applicable entities. Moreover, a provider can save time using the AI assisted clinical decision support system to automatically select a medical indication for an order that has a high probability of corresponding to the order or by narrowing down a database of numerous possible medical indications to a manageable number of likely possibilities that the provider can quickly review and select from. Some government regulations require that providers use some sort of decision support mechanism when selecting a medical indication and/or an Appropriate Use Criteria (AUC) for an order. The AI assisted clinical decision support system, according to some embodiments of the inventive concept described herein, may allow providers to comply with governmental regulations requiring the use of some type of clinical decision support mechanism for their orders.

Referring to FIG. 1, a communication network 100 including an AI assisted clinical decision support system for determining a medical indication for an order, in accordance with some embodiments of the inventive concept, comprises a health care facility server 105 that is coupled to devices 110a, 110b, and 110c via a network 115. The health care facility may be any type of health care or medical facility, such as a hospital, doctor's office, specialty center (e.g., surgical center, orthopedic center, laboratory center etc.), or the like. The health care facility server 105 may be configured with an Electronic Medical Record (EMR) system module 120 to manage patient files and facilitate the entry of orders for patients via health care service providers ("providers"). Although shown as one combined system in FIG. 1, it will be understood that some health care facilities use separate systems for electronic medical record management and order entry management. The providers may use devices, such as devices 110a, 110b, and 110c to manage patients' electronic records and to issue orders for the patients through the EMR system 120. An order may include, but is not limited to, a treatment, a procedure (e.g., surgical procedure, physical therapy procedure, radiologic/imaging procedure, etc.) a test, a prescription, and the like. The network 115 communicatively couples the devices 110a, 110b, and 110c to the health care facility server 105. The network 115 may comprise one or more local or wireless networks to communicate with the health care facility server 105 when the health care facility server 105 is located in or proximate to the health care facility. When the health care facility server 105 is in a remote location from the health care facility, such as part of a cloud computing system or at a central computing center, then the network 115 may include one or more wide area or global networks, such as the Internet.

According to some embodiments of the inventive concept, providers may access an AI assisted clinical decision support system to assist them in selecting a medical indication for a patient order. The AI assisted medical indication selection support system may include a health care facility interface server 130, which includes an EMR interface/clinical decision support (CDS) system module 135 to facilitate the transfer of information between the EMR system 120, which the providers use to manage patient records and issue orders, and an AI server 140, which includes an AI engine module 145. The AI server 140 and AI engine module 145 may be configured to receive patient information, provider information, and order information contained in records in the EMR system 120 from the health care facility server 105 and EMR system module 120 by way of the health care facility interface server 130 and EMR interface/CDS system module 135. The EMR interface/CDS system module 135 in conjunction with the AI engine module 145 may be further configured to generate a recommendation of one or more possible medical indications for the order when the recommendation can be supported by evidence-based guidelines used by the AI engine module 145. It will be understood that the division of functionality described herein between the AI server/AI engine module 145 and the health care facility interface server 130/EMR interface/CDS system module 135 is an example. Various functionality and capabilities can be moved between the AI server/AI engine module 145 and the health care facility interface server 130/EMR interface/CDS system module 135 in accordance with different embodiments of the inventive concept. Moreover, in some embodiments, the AI server/AI engine module 145 and the health care facility interface server 130/EMR interface/CDS system module 135 may be merged as a single logical and/or physical entity.

A network 150 couples the health care facility server 105 to the health care facility interface server 130. The network 150 may be a global network, such as the Internet or other publicly accessible network. Various elements of the network 150 may be interconnected by a wide area network, a local area network, an Intranet, and/or other private network, which may not be accessible by the general public. Thus, the communication network 150 may represent a combination of public and private networks or a virtual private network (VPN). The network 150 may be a wireless network, a wireline network, or may be a combination of both wireless and wireline networks.

The service provided through the health care facility interface server 130, EMR interface/CDS system module 135, AI server 140 and AI engine module 145 to provide AI assisted clinical decision support for patient orders may, in some embodiments, be embodied as a cloud service. For example, health care facilities may integrate their EMR systems/order systems with the AI assisted clinical decision support service and access the service as a Web service. In some embodiments, the AI assisted clinical decision support service may be implemented as a Representational State Transfer Web Service (RESTful Web service).

Although FIG. 1 illustrates an example communication network including an AI assisted clinical decision support system for determining a medical indication for an order, it will be understood that embodiments of the inventive subject matter are not limited to such configurations, but are intended to encompass any configuration capable of carrying out the operations described herein.

Figure 2:
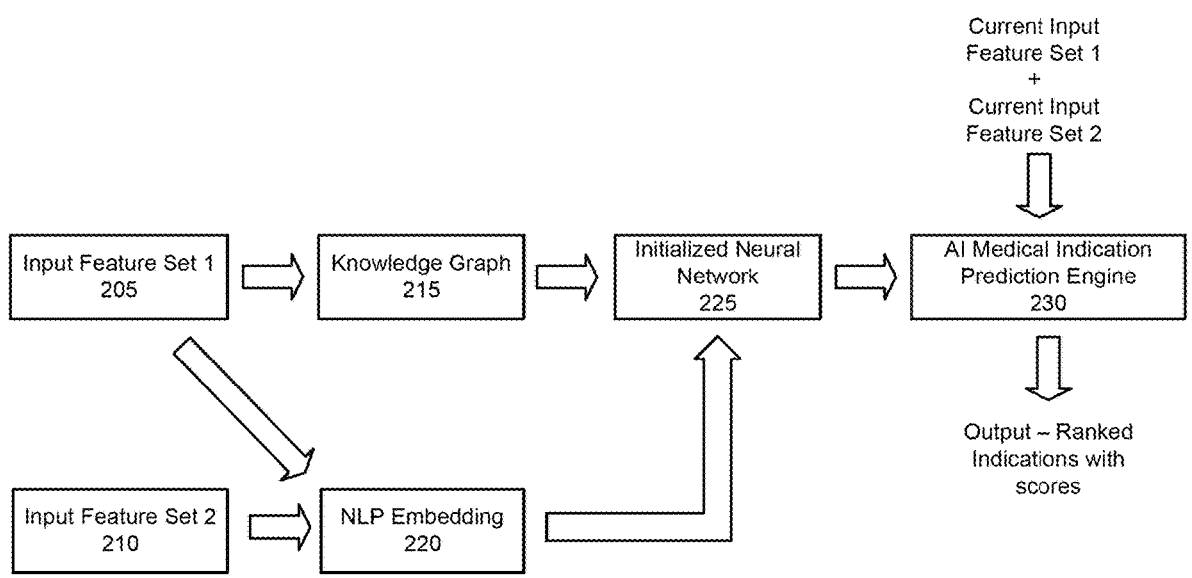
FIG. 2 is a block diagram of an AI engine used in the AI assisted clinical decision support system of FIG. 1 in accordance with some embodiments of the inventive concept.

FIG. 2 is a block diagram of an AI engine used in the AI assisted clinical decision support system of FIG. 1 in accordance with some embodiments of the inventive concept. As shown in FIG. 2, the AI engine 145 may be configured to receive two different types of input information, which are identified as input feature set 1 205 and input feature set 2 210. Input feature set 1 205 may represent patient, provider, and/or order information. The patient information may include, but is not limited to, age, gender, problem list, encounter diagnosis, patient class, and/or a medical center department. The provider information may include, but is not limited to, a provider identifier and/or a provider specialty. The scope of recognition for the provider identifier may span a range of possibilities. For example, the provider identifier may be a site-specific (e.g., hospital or medical practice specific), regional, and/or national identifier. The order information may include, but is not limited to, an order name, order identification, order modality, order contrast, and/or body area identification. Input feature set 2, 210 may comprise one or more free-text queries or reasons for the order generated by one or more medical practitioners. Examples of such queries or reasons may include observations by a medical professional and/or complaints by a patient, such as, but not limited to, pain, intoxicated, altered mental status, nausea, lack of energy, etc. The input feature set 1 205 variables may be used to generate a knowledge graph 215, which defines the relationships between the input feature set 1 205 variables and medical indications. These relationships are visualized as a graph structure including nodes and edges that connect the nodes. The nodes of the knowledge graph may then be used to define a neural network, which can be trained to generate recommendations for medical indications based on an aggregated vector of the input feature set 1 205 variables and the input feature set 2 210 free-text query or reason.

The input feature set 2 210 including the free-text query or reason may be processed using a natural language processing embedding module 220 to generate a free-text query vector for the free-text query or reason. Other variables from input feature set 1 205 may also be processed using the natural language processing embedding module 220 to generate vectors therefor. As described above, an embedding is a learned continuous vector representation of a discrete variable. These variables from input feature set 1 205 may be categorical or discrete variables for which a continuous vector is generated. The NLP embedding module 220 may also generate vectors for each of the medical indications that may be recommended or identified through the clinical decision support system.

Figure 3:
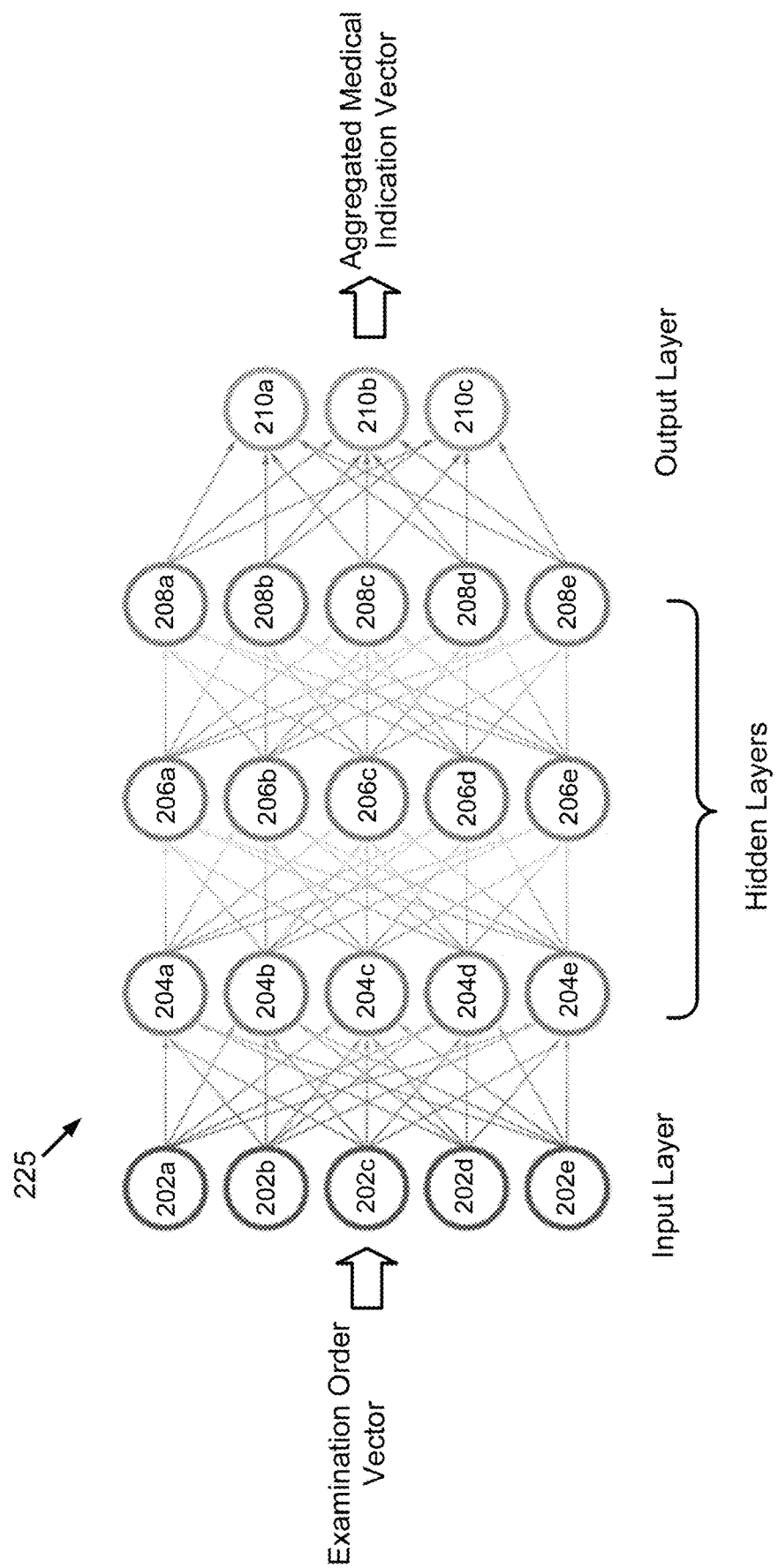
FIG. 3 is a block diagram of a neural network used in the AI engine of FIGS. 1 and 2 in accordance with some embodiments of the inventive concept.

A neural network 225 is generated based on the knowledge graph 215 and may be initialized with the input variable vectors corresponding to the input feature set 1 205 variables along with the free-text query or reason vector generated based on the input feature set 2 210 information. FIG. 3 is a diagram of an initialized artificial neural network system 225 according to some embodiments of the inventive concept. As shown in FIG. 3, the artificial neural network 225 includes a plurality of node layers comprising an input layer, one or more hidden layers, and an output layer. In the example shown in FIG. 2, an input layer comprises five nodes or neurons 202*a*, 202*b*, 202*c*, 202*d*, and 202*e* and an output layer comprises three nodes or neurons 210*a*, 210*b*, and 210*c*. In the example shown, three hidden layers connect the input layer to the output layer including a first hidden layer comprising five nodes or neurons 204*a*, 204*b*, 204*c*, 204*d*, and 204*e*, a second hidden layer comprising five nodes or neurons 206*a*, 206*b*, 206*c*, 206*d*, and 206*e*, and a third hidden layer comprising five nodes or neurons 208*a*, 208*b*, 208*c*, 208*d*, and 208*e*. Other embodiments may use more or fewer hidden layers. Each node or neuron connects to another and has an associated weight and threshold. If the output of any individual node or neuron is above the specified threshold value, that node is activated, sending data to the next layer of the network. Otherwise, no data is passed along to the next layer of the network.

The number of nodes in the input layer 202*a*, 202*b*, 202*c*, 202*d*, and 202*e* may correspond to the number of variables in the input feature set 1 205 and the input feature set 2 210. In aggregate, the embedded vectors corresponding to the input feature set 1 205 and the input feature set 2 210 variables and free-text queries or reason(s) may be viewed as an examination order vector. The number of nodes in the output layer 210*a*, 210*b*, and 210*c* may correspond to the number of different medical indications that may be recommended or identified using the neural network 225. In aggregate, the embedded vectors of the different medical indications may be viewed as an aggregated medical indication vector.

As described above, the artificial neural network 225 relies on training data to learn and improve its accuracy over time. The neural network 225 may be trained to determine one or more medical indications that may be applicable to an examination order based on evidence-based guidelines provided by, for example, one or more medical specialty societies, medical schools, government regulations, and the like. These guidelines may be used in the training, knowledge base, and/or vocabulary for the neural network 225 and the natural language processor embedding module 220. Once the various parameters of the neural network system 225 are tuned and refined for accuracy, it can be used, among other applications, to generate inferences or recommendations for medical indications in response to input data associated with a patient, provider, and/or order, including free-text queries or reasons provided by a medical practitioner where the recommendation(s) can be supported by the evidence-based guidelines. Such a neural network 225 may also be trained to perform other tasks, such as, but not limited to, classify images, recognize and interpret speech, and cluster data, amongst other uses.

Each individual node or neuron may be viewed as implementing a linear regression model, which is composed of input data, weights, a bias (or threshold), and an output. Once an input layer is determined, weights are assigned. These weights help determine the importance of any given variable, with larger ones contributing more significantly to the output compared to other inputs. All inputs are then multiplied by their respective weights and then summed, i.e., a MAC operation. In FIG. 3, node or neuron 206a, for example, receives inputs corresponding to the outputs of nodes or neurons 204a, 204b, 204c, 204d, and 204e. These inputs are multiplied by their corresponding weights and summed at node or neuron 206a. Afterward, the output is passed through an activation function, which determines the output. If that output exceeds a given threshold, it activates the node by passing data to the next layer in the network. This results in the output of one node becoming in the input of the next node. This process of passing data from one layer to the next layer is an example of a feedforward artificial neural network. Some embodiments of the inventive concept may provide a rectified linear unit (ReLU) activation function for use at one or more of the neural network 225 nodes.

Returning to FIG. 2, the trained initialized neural network 225 may be used as an AI medical indication prediction engine 230 in which a user provides new information or data corresponding to one or more of the input feature set 1 205 variables and/or the input feature set 2 210 free-text queries or reasons as input. The AI medical indication prediction engine 230 may generate an output comprising one or more ranked medical indications based on similarity scores. The similarity scores may be indicative of a similarity between the examination order vector, which comprises an aggregation of the input variable vectors and the free-text query vector, and an aggregated medical indication vector, which comprises an aggregation of the medical indication vectors from the output layer 210a, 210b, 210c of the neural network 225. The individual similarity scores may be based on the similarity between the examination order vector and the individual medical indication vectors from the output layer 210a, 210b, 210c. In some embodiments, cosine similarity score(s) may be generated between the examination order vector and the aggregated medical indication vector and/or the individual medical indication vector and used to rank the various medical indications in terms based on their probability of being relevant or applicable responsible to the input feature set 1 and input feature set 2 information.

Figure 4:
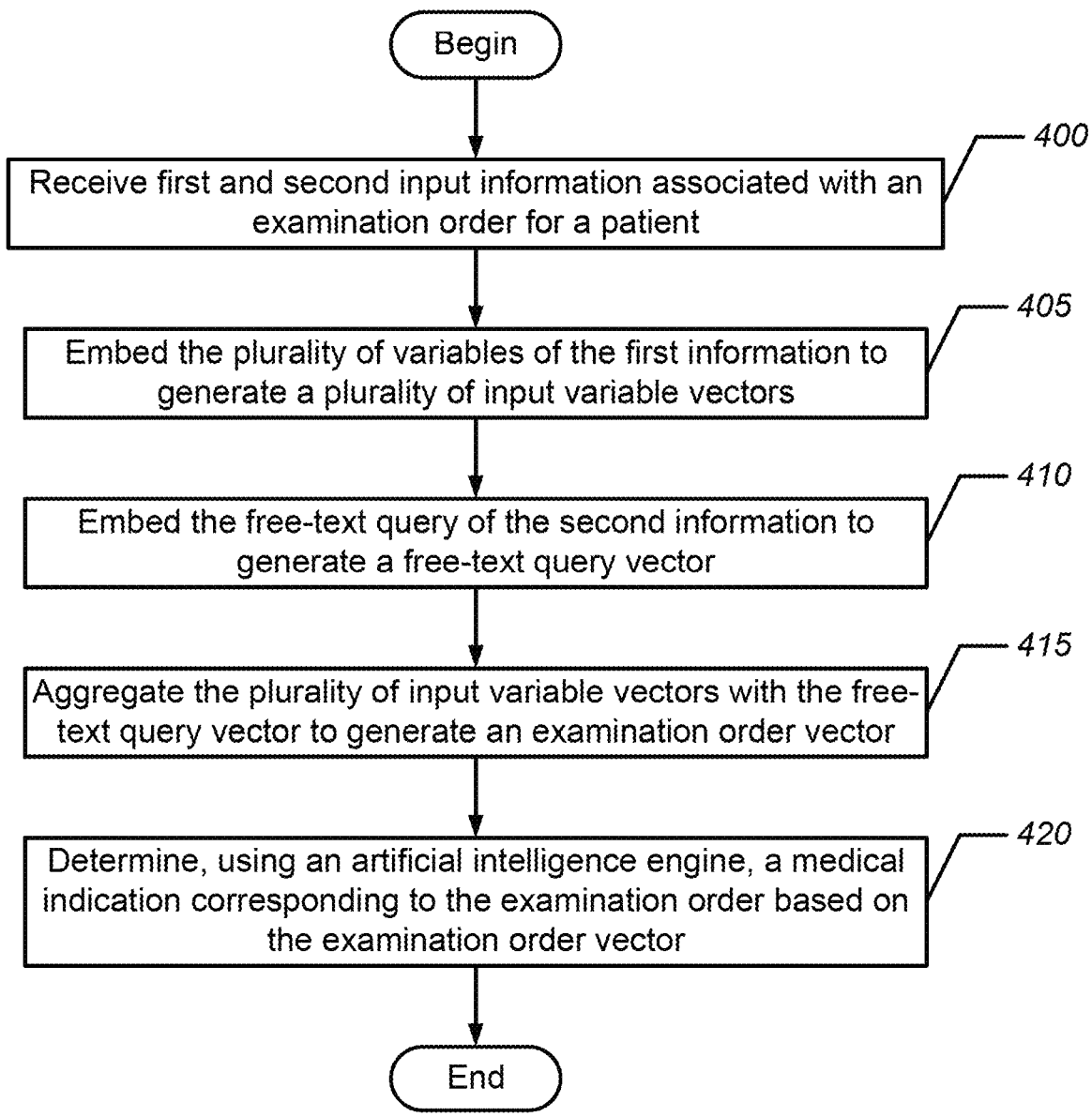
FIGS. 4-6 are flowcharts that illustrate operations for determining a medical indication for an order using the AI assisted clinical decision support system of FIG. 1 in accordance with some embodiments of the inventive concept.
Figure 5:
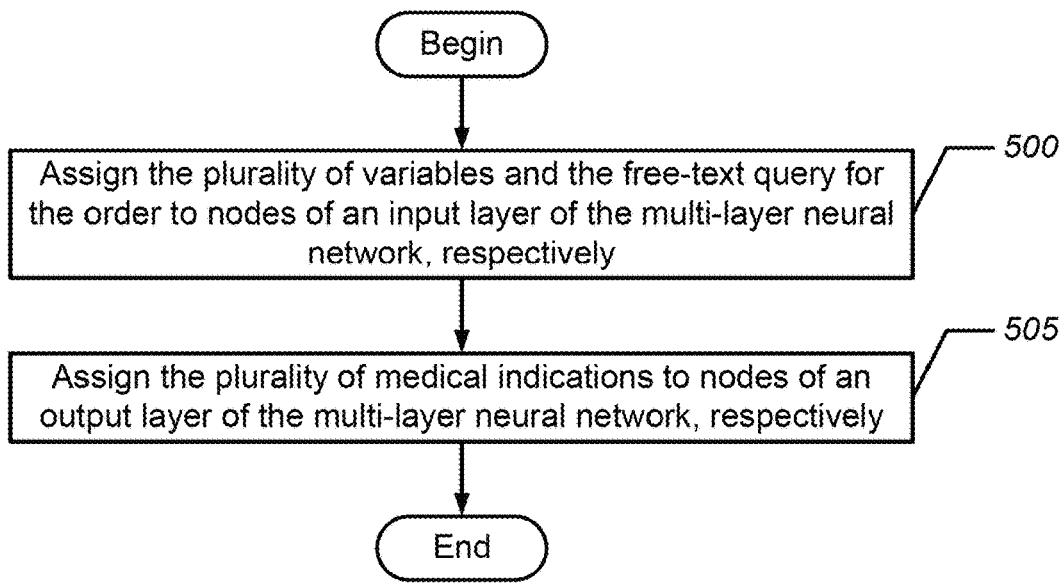
Figure 6:
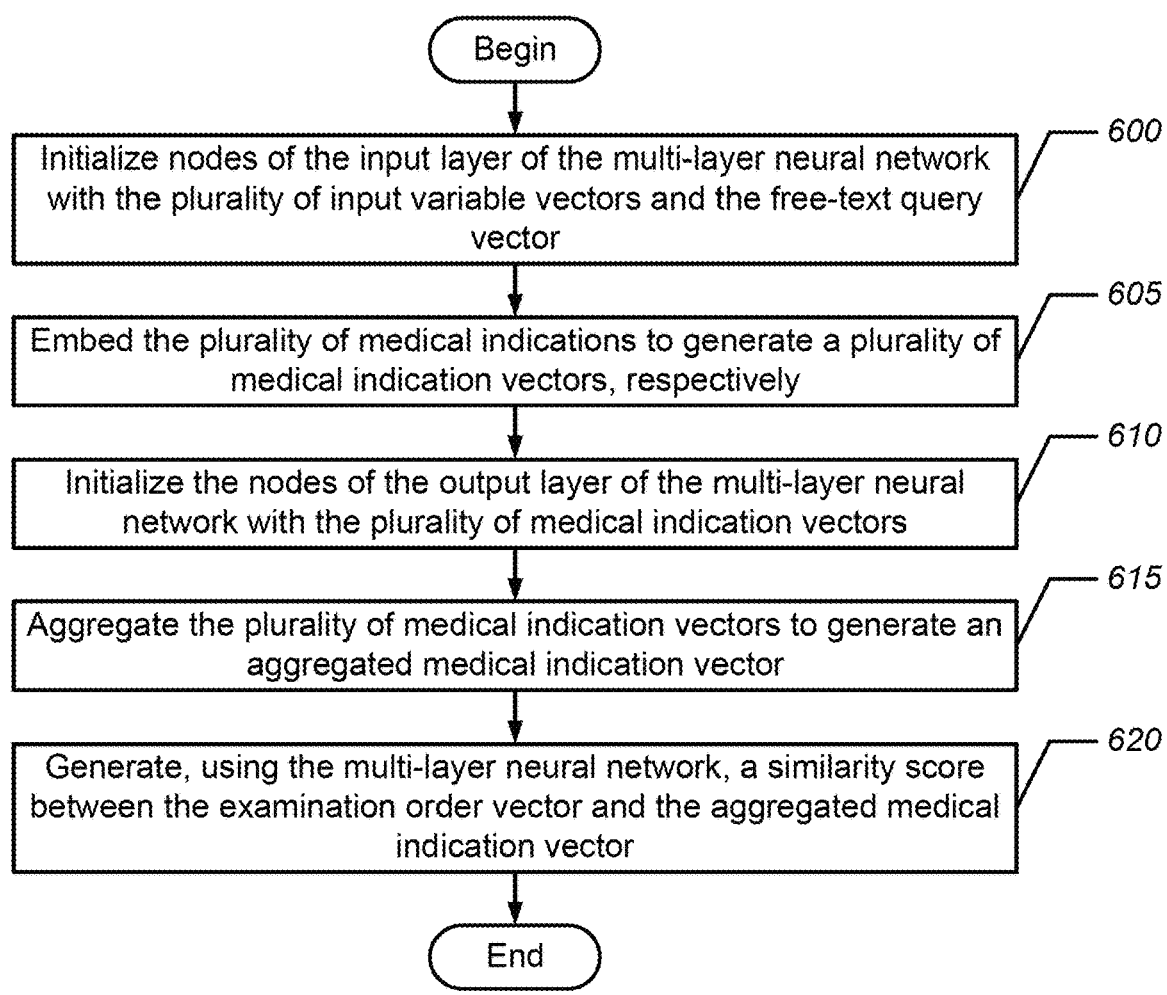

FIGS. 4-6 are flowcharts that illustrate operations for determining a medical indication for an order using the AI assisted clinical decision support system of FIG. 1 in accordance with some embodiments of the inventive concept. Referring now to FIG. 4, operations begin at block 400 where first and second information associated with an examination order is received. The first information may be, for example, one or more input variable values for the input variable of feature set 1 205 described above and the second information may be, for example, one or more free-text queries or reason(s) for the input feature set 2 210 described above. The plurality of variables of the first information may be embedded using the natural language process embedding module 220 to generate a plurality of input variable vectors, respectively, at block 405. One or more of the free-text queries or reasons of the second information may be embedded at block 410 to generate a free-text query vector. The plurality of input variable vectors may be aggregated with the free-text query vector to generate an examination order vector at block 415. An artificial intelligence engine, such as the neural network 225 may be used at block 420 to determine a medical indication that corresponds to the examination order based on the examination order vector.

Referring now to FIG. 5, example operations of the neural network 225 begin at block 500 where the plurality of variables and the free-text query are assigned to the input layer nodes of the neural network 225. The plurality of medical indications is assigned to nodes of the output layer of the neural network 225 at block 505. Referring now to FIG. 6, the nodes of the input layer of the neural network 225 are initialized with the plurality of input variable vectors and the free-text query vector at block 600. The plurality of medical indications is embedded using, for example, the natural language processing module 220, at block 605 to generate a plurality of medical indication vectors, respectively. The nodes of the output layer of the neural network 225 are initialized with the plurality of medical indication vectors, respectively, at block 610. The plurality of medical indication vectors is aggregated to generate an aggregated medical indication vector at block 615. A similarity score between the examination order vector and the aggregated medical indication vector may be generated at block 620 using the neural network 225. The similarity score may be, for example, a cosine similarity score in some embodiments of the inventive concept. A plurality of similarity scores may be generated between the examination order vector and the individual medical indication vectors, which are indicative of the probability that the medical indication is relevant or applicable to the examination order vector, which is based on heterogeneous information including input variable information (e.g., input feature set 1 205 information) as well as one or more free-text queries or reasons (e.g., input feature set 2 210).

The similarity scores (e.g., cosine similarity scores) are indicative of the probabilities that respective ones of the medical indications are applicable to an examination order. Thus, in some embodiments, when a particular medical indication has a similarity score corresponding to a probability that exceeds a defined threshold for an examination order, then the medical indication may be communicated, for example, to the health care facility server 105 and order entry system/EMR system 120 for automatic entry therein thereby alleviating the provider of having to select a medical indication for the order.

There may not be a single medical indication, however, having a probability applicability to the examination order that exceeds the defined threshold for automatic selection.

According to some embodiments of the inventive concept, the list of possible medical indications for a provider to consider may be narrowed by communicating to the health care facility server 105 and order entry system/EMR system 120 by way of the AI server/AI engine module 145 and the health care facility interface server 130/EMR interface/CDS system module 135 a list of medical indications having the N highest probabilities of being applicable to the examination order based on their similarity scores. The number N may be selected to provide a manageable number of medical indications for a provider to review and may also be determined based on cut-offs or gaps between the similarity scores associated with possible medical indications.

The probabilities associated with the highest probable medical indications may, however, be relatively low. This may indicate that the neural network 225 was unable to find a medical indication for an examination order that satisfies the evidence-based guidelines on which the neural network 225 is trained. Thus, when a highest probability corresponding to one of the possible medical indications is below a defined threshold (e.g., the similarity score is below a defined threshold) or, in other embodiments, when a sum of the probabilities of the K possible medical indications having the highest probabilities is below a defined threshold (e.g., a sum of the similarity scores of the K possible medical indications having the highest probabilities is below a defined threshold), then it can be concluded that no medical indication was found for that particular examination order. This "no result" outcome can be communicated to the health care facility server 105 and order entry system/EMR system 120 to allow the provider to select a medical indication manually.

Figure 7:
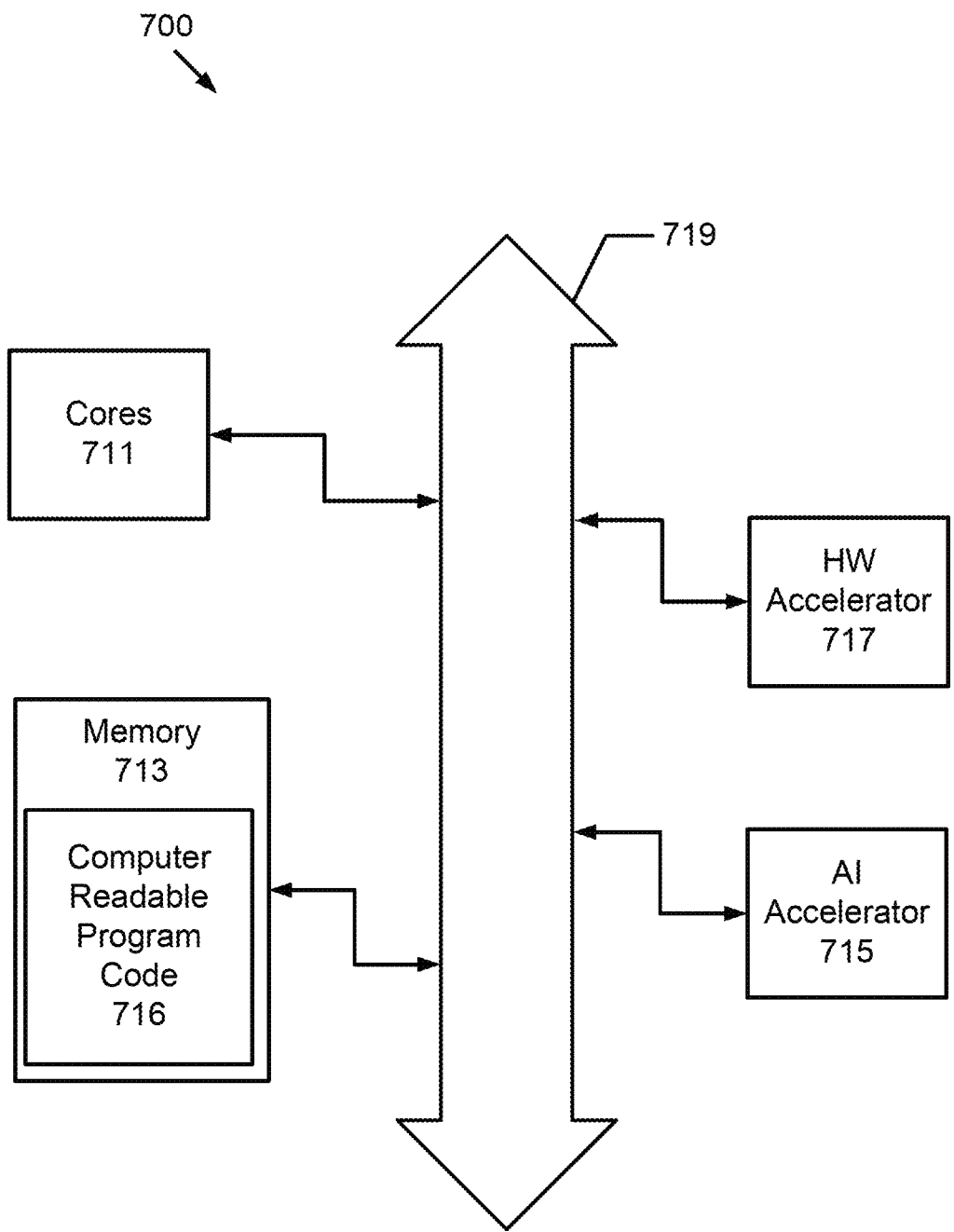
FIG. 7 is a data processing system that may be used to implement an AI assisted clinical decision system in accordance with some embodiments of the inventive concept.

FIG. 7 is a block diagram of a data processing system 700 that may be used to implement the AI server 140 of FIG. 1, in accordance with some embodiments of the inventive concept. As shown in FIG. 7, the data processing system 700 may include at least one core 711, a memory 713, an Artificial Intelligence (AI) accelerator 715, and a hardware (HW) accelerator 717. The at least one core 711, the memory 713, the AI accelerator 715, and the HW accelerator 717 may communicate with each other through a bus 719.

The at least one core 711 may be configured to execute computer program instructions. For example, the at least one core 711 may execute an operating system and/or applications represented by the computer readable program code 716 stored in the memory 713. In some embodiments, the at least one core 711 may be configured to instruct the AI accelerator 715 and/or the HW accelerator 717 to perform operations by executing the instructions and obtain results of the operations from the AI accelerator 715 and/or the HW accelerator 717. In some embodiments, the at least one core 711 may be an ASIP customized for specific purposes and support a dedicated instruction set.

The memory 713 may have an arbitrary structure configured to store data. For example, the memory 713 may include a volatile memory device, such as dynamic random-access memory (DRAM) and static RAM (SRAM), or include a non-volatile memory device, such as flash memory and resistive RAM (RRAM). The at least one core 711, the AI accelerator 715, and the HW accelerator 717 may store data in the memory 713 or read data from the memory 713 through the bus 719.

The AI accelerator 715 may refer to hardware designed for AI applications. In some embodiments, the AI accelerator 715 may include clinical decision support system functionality configured to provide one or more recommendations for medical indications based on heterogeneous input data including one or more free-text queries or reasons generated by a provider. The AI accelerator 715 may generate output data by processing input data provided from the at least one core 715 and/or the HW accelerator 717 and provide the output data to the at least one core 711 and/or the HW accelerator 717. In some embodiments, the AI accelerator 715 may be programmable and be programmed by the at least one core 711 and/or the HW accelerator 717. The HW accelerator 717 may include hardware designed to perform specific operations at high speed. The HW accelerator 717 may be programmable and be programmed by the at least one core 711.

Figure 8:
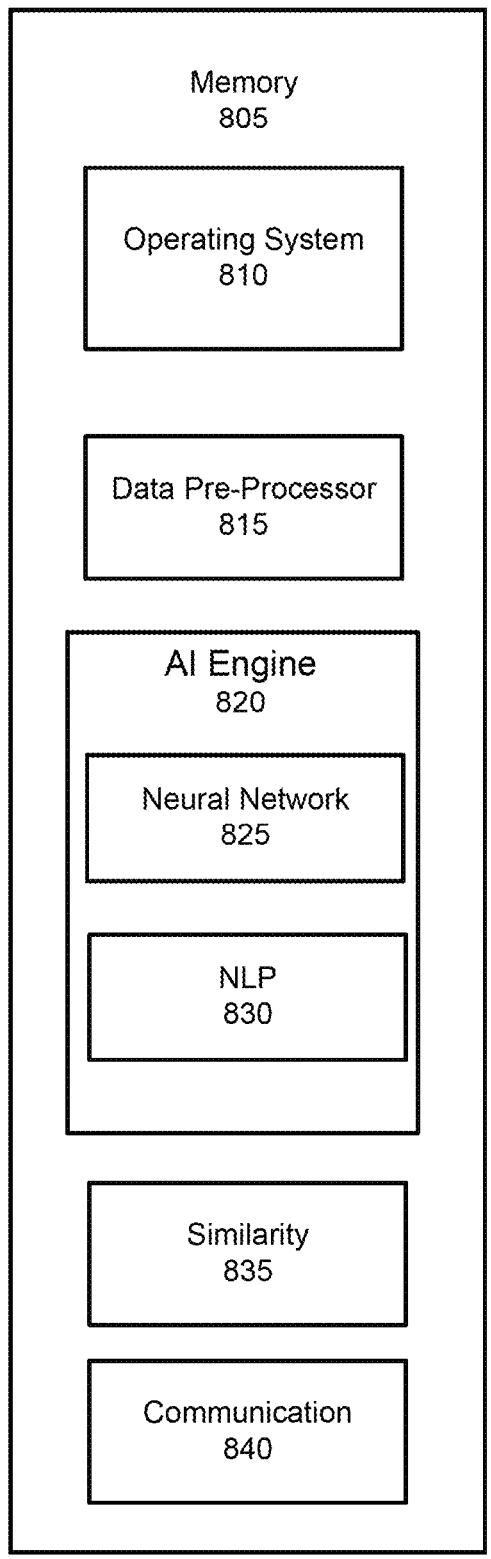
FIG. 8 is a block diagram that illustrates a software/hardware architecture for use in the AI assisted clinical decision support system of FIG. 1 in accordance with some embodiments of the inventive concept.

FIG. 8 illustrates a memory 805 that may be used in embodiments of data processing systems, such as the AI server 140 of FIG. 1 and the data processing system 700 of FIG. 7, respectively, to facilitate operation of an AI assisted clinical decision support system that operates on an aggregation of heterogeneous input data. The memory 805 is representative of the one or more memory devices containing the software and data used for facilitating operations of the AI server 140 as described herein. The memory 805 may include, but is not limited to, the following types of devices: cache, ROM, PROM, EPROM, EEPROM, flash, SRAM, and DRAM. As shown in FIG. 8, the memory 805 may contain five or more categories of software and/or data: an operating system 810, a data pre-processor module 815, an AI engine 820, a similarity module 835, and a communication module 840. In particular, the operating system 810 may manage the data processing system's software and/or hardware resources and may coordinate execution of programs by the processor.

The data pre-processor may be configured to receive and organize the information corresponding to the input feature set 1 205 and the input feature set 2 210 when the neural network 225 is in training mode and when the neural network 225 is in inference, decision, and/or recommendation mode. The AI engine module 820 may comprise a neural network module 825 and a natural language processing module 830. The neural network module 825 may be configured to perform one or more of the operations described above with respect to the neural network 225 and FIGS. 4-6. The natural language processing module 830 may be configured to perform one or more of the operations described above with respect to the natural language processing embedding module 220 and FIGS. 4-6. The similarity module 835 may be configured to implement similarity evaluation functionality, such cosine similarity functionality including one or more of the operations described above with respect to FIGS. 2-6. The communication module 840 may be configured to facilitate communication between the AI server 140 of FIG. 1 and entities, such as providers, insurance claim payors, clinical researchers, and the like.

Although FIGS. 7 and 8 illustrate hardware/software architectures that may be used in data processing systems, such as the AI server 140 of FIG. 1 and the data processing system 700 of FIG. 7, respectively, in accordance with some embodiments of the inventive concept, it will be understood that the present invention is not limited to such a configuration but is intended to encompass any configuration capable of carrying out operations described herein.

Computer program code for carrying out operations of data processing systems discussed above with respect to FIGS. 1-8 may be written in a high-level programming language, such as Python, Java, C, and/or C++, for development convenience. In addition, computer program code for carrying out operations of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Moreover, the functionality of the AI server 140 of FIG. 1 and the data processing system 700 of FIG. 7 may each be implemented as a single processor system, a multi-processor system, a multi-core processor system, or even a network of stand-alone computer systems, in accordance with various embodiments of the inventive concept. Each of these processor/computer systems may be referred to as a "processor" or "data processing system." The functionality provided by the health care facility interface server 130 and the AI server 140 may be merged into a single server or maintained as separate servers in accordance with different embodiments of the inventive concept.

The data processing apparatus described herein with respect to FIGS. 1-8 may be used to facilitate operation of a clinical decision support system that supports medical indication determination using heterogeneous data according to some embodiments of the inventive concept described herein. These apparatus may be embodied as one or more enterprise, application, personal, pervasive and/or embedded computer systems and/or apparatus that are operable to receive, transmit, process and store data using any suitable combination of software, firmware and/or hardware and that may be standalone or interconnected by any public and/or private, real and/or virtual, wired and/or wireless network including all or a portion of the global communication network known as the Internet, and may include various types of tangible, non-transitory computer readable media. In particular, the memory 805 when coupled to a processor includes computer readable program code that, when executed by the processor, causes the processor to perform operations including one or more of the operations described herein with respect to FIGS. 1-6.

Some embodiments of the inventive concept may provide an AI assisted clinical decision support service that uses relevant heterogeneous data about the patient, provider, and/or examination order context (e.g., free-text query or reason provided by a health care professional) to predict the most likely medical indications that would be relevant for the patient, provider, and/or examination order scenario. The clinical decision support system may aggregate the heterogenous input data to train the AI system (e.g., train a multi-layer neural network) and as input to the AI system when the AI system is in decision or recommendation mode. By aggregating the heterogeneous input data for training the AI system and generating decisions or recommendation, the accuracy of the AI system may be improved relative to systems that use separate AI models or systems (e.g., a neural network and a natural language processing system) whose outputs are combined through weighted averaging or other techniques for a final decision or recommendation.

The clinical decision support system, according to some embodiments of the inventive concept, may simplify and improve a provider's workflow in a health care facility and may improve the quality of care and patient outcomes in one or more of the following ways: predicting or recommending medical indications for an examination order with high specificity; ensuring regulatory compliance/appropriateness of an order by using a clinical decision support system in choosing a medical indication; identifying the most appropriate order with relatively high probability for a patient and/or reducing or eliminating unnecessary orders/tests for a patient; and making a provider's workflow more efficient and less time consuming as reviewing hundreds or thousands of possible medical indications can be avoided with the AI assisted clinical decision support system reducing the number of medical indications to review to a manageable number or even automatically selecting the most likely medical indication when the probability of that medical indication being appropriate to the order exceeds a threshold.

Further Definitions and Embodiments

In the above description of various embodiments of the present inventive concept, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

The flowchart and block diagrams in the figures illustrate the architecture, functionality, and operation of possible implementations of systems, methods, and computer program products according to various aspects of the present inventive concept. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

In the above-description of various embodiments of the present inventive concept, aspects of the present inventive concept may be illustrated and described herein in any of a number of patentable classes or contexts including any new and useful process, machine, manufacture, or composition of matter, or any new and useful improvement thereof. Accordingly, aspects of the present inventive concept may be implemented entirely hardware, entirely software (including firmware, resident software, micro-code, etc.) or combining software and hardware implementation that may all generally be referred to herein as a "circuit," "module," "component," or "system." Furthermore, aspects of the present inventive concept may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

The description of the present inventive concept has been presented for purposes of illustration and description, but is not intended to be exhaustive or limited to the inventive concept in the form disclosed. Many modifications and variations will be apparent to those of ordinary skill in the art without departing from the scope and spirit of the inventive concept. The aspects of the inventive concept herein were chosen and described to best explain the principles of the inventive concept and the practical application, and to enable others of ordinary skill in the art to understand the inventive concept with various modifications as are suited to the particular use contemplated.

What is claimed is:

1. A computer-implemented method, comprising:
   receiving, by one or more processors, input information associated with an examination order for a patient, the input information comprising first information associated with a plurality of variables and second information associated with a free-text query for the examination order;
   generating, by the one or more processors and a first artificial intelligence (AI) model based on the plurality of variables, a plurality of variable vectors, respectively;
   generating, by the one or more processors and a second AI model based on the free-text query, a free-text query vector;
   aggregating, by the one or more processors, the plurality of variable vectors with the free-text query vector to generate an examination order vector;
   generating, by the one or more processors, a knowledge graph associating the plurality of variables with a plurality of medical indications;
   initializing, by the one or more processors, a neural network based at least in part on the knowledge graph;
   determining, by the one or more processors and the neural network and based on the examination order vector, a set of medical indications corresponding to the examination order; and
   automatically storing, by the one or more processors, an indication of the set of medical indications in an electronic medical record system.

2. The computer-implemented method of claim 1, further comprising:
   assigning, by the one or more processors, the plurality of variables and the free-text query for the examination order to nodes of an input layer of the neural network, respectively; and
   assigning, by the one or more processors, the plurality of medical indications to nodes of an output layer of the neural network, respectively.

3. The computer-implemented method of claim 2, further comprising:
   initializing, by the one or more processors, the nodes of the input layer of the neural network with the plurality of variable vectors and the free-text query vector;
   embedding, by the one or more processors, the plurality of medical indications to generate a plurality of medical indication vectors, respectively; and
   initializing, by the one or more processors, the nodes of the output layer of the neural network with the plurality of medical indication vectors;
   wherein determining, by the one or more processors and the neural network and based on the examination order vector, the sete of medical indications comprises:
      aggregating, by the one or more processors, the plurality of medical indication vectors to generate an aggregated medical indication vector; and
      generating, by the one or more processors and using the neural network, a similarity score between the examination order vector and the aggregated medical indication vector.

4. The computer-implemented method of claim 3, wherein generating the similarity score comprises:
   generating, by the one or more processors and using the neural network, a plurality of similarity scores between the examination order vector and the plurality of medical indication vectors, respectively.

5. The computer-implemented method of claim 4, wherein generating the plurality of similarity scores comprises:
   generating, by the one or more processors and using the neural network, a plurality of cosine similarity scores between the examination order vector and the plurality of medical indication vectors, respectively.

6. The computer-implemented method of claim 5, wherein the set of medical indications corresponding to the examination order comprises one of the plurality of medical indications having a highest ranked similarity score associated therewith.

7. The computer-implemented method of claim 6, further comprising:
   transmitting, by the one or more processors, to an examination order entry system for entry therein, without input from a provider, an automatic selection of the one of the plurality of medical indications having the highest ranked similarity score associated therewith in response to determining that a highest ranked cosine similarity score of the plurality of cosine similarity scores meets or exceeds a threshold score.

8. The computer-implemented method of claim 5, wherein the set of medical indications corresponding to the examination order comprises N of the plurality of medical indications having N highest ranked cosine similarity scores of the plurality of cosine similarity scores associated therewith, the method further comprising:
  transmitting, by the one or more processors, to an examination order entry system the N of the plurality of medical indications having the N highest ranked cosine similarity scores associated therewith, respectively, in response to determining that a highest ranked cosine similarity score of the plurality of cosine similarity scores does not meet or exceed a threshold score;
  wherein N is one or more and less than a total number of the plurality of medical indications.

9. The computer-implemented method of claim 5, wherein the set of medical indications corresponding to the examination order comprises none of the plurality of medical indications, the method further comprising:
  transmitting, by the one or more processors, to an examination order entry system an indication that none of the plurality of medical indications are applicable to the examination order in response to determining that a highest ranked cosine similarity score of the plurality of cosine similarity scores is less than a threshold score.

10. The computer-implemented method of claim 1, wherein the plurality of variables comprises one or more variables associated with the patient including at least one of an age, a gender, a problem list, an encounter diagnosis, a patient class, or a medical center department;
  wherein the plurality of variables comprises one or more variables associated with a provider including at least one of a provider identifier or a provider specialty; and
  wherein the plurality of variables comprises at least one of an examination order name, an examination order identification, an examination order modality, an examination order contrast, or a body area identification.

11. A system, comprising:
  one or more processors; and
  at least one memory storing computer readable program code that is executable by the one or more processors to perform operations comprising:
  receiving input information associated with an examination order for a patient, the input information comprising first information associated with a plurality of variables and second information associated with a free-text query for the examination order;
  generating, by a first artificial intelligence (AI) model based on the plurality of variables, a plurality of variable vectors, respectively;
  generating, by a second AI model based on the free-text query, a free-text query vector;
  aggregating the plurality of variable vectors with the free-text query vector to generate an examination order vector;
  generating a knowledge graph associating the plurality of variables with a plurality of medical indications;
  initializing a neural network based at least in part on the knowledge graph;
  determining, by the neural network and based on the examination order vector, a set of medical indication corresponding to the examination order; and
  automatically storing an indication of the set of medical indications in an electronic medical record system.

12. The system of claim 11, wherein the operations further comprise:
  assigning the plurality of variables and the free-text query for the examination order to nodes of an input layer of the neural network, respectively; and
  assigning the plurality of medical indications to nodes of an output layer of the neural network, respectively.

13. The system of claim 12, wherein the operations further comprise:
  initializing the nodes of the input layer of the neural network with the plurality of variable vectors and the free-text query vector;
  embedding the plurality of medical indications to generate a plurality of medical indication vectors, respectively; and
  initializing the nodes of the output layer of the neural network with the plurality of medical indication vectors;
  wherein determining, by the neural network and based on the examination order vector, the set of medical indications comprises:
    aggregating the plurality of medical indication vectors to generate an aggregated medical indication vector; and
    generating, using the neural network, a similarity score between the examination order vector and the aggregated medical indication vector.

14. The system of claim 13, wherein generating the similarity score comprises:
  generating, using the neural network, a plurality of similarity scores between the examination order vector and the plurality of medical indication vectors, respectively.

15. One or more non-transitory computer readable storage media comprising computer readable program code stored in the media that is executable by one or more processors to perform operations comprising:
  receiving input information associated with an examination order for a patient, the input information comprising first information associated with a plurality of variables and second information associated with a free-text query for the examination order;
  generating, by a first artificial intelligence (AI) model based on the plurality of variables, a plurality of variable vectors, respectively;
  generating, by a second AI model based on the free-text query, a free-text query vector;
  aggregating the plurality of variable vectors with the free-text query vector to generate an examination order vector;
  generating a knowledge graph associating the plurality of variables with a plurality of medical indications;
  initializing a neural network based at least in part on the knowledge graph;
  determining, by the neural network and based on the examination order vector, a set of medical indications corresponding to the examination order; and
  automatically storing an indication of the set of medical indications in an electronic medical record system.

16. The one or more non-transitory computer readable storage media of claim 15, wherein, the operations further comprise:
  assigning the plurality of variables and the free-text query for the examination order to nodes of an input layer of the neural network, respectively; and
  assigning the plurality of medical indications to nodes of an output layer of the neural network, respectively.

17. The one or more non-transitory computer readable storage media of claim 16, wherein the operations further comprise:

initializing the nodes of the input layer of the neural network with the plurality of variable vectors and the free-text query vector;
embedding the plurality of medical indications to generate a plurality of medical indication vectors, respectively; and
initializing the nodes of the output layer of the neural network with the plurality of medical indication vectors;
wherein determining, by the neural network and based on the examination order vector, the set of medical indications comprises:
aggregating the plurality of medical indication vectors to generate an aggregated medical indication vector; and
generating, using the neural network, a similarity score between the examination order vector and the aggregated medical indication vector.

* * * * *